United States Patent [19]

Enjoji et al.

[11] 4,289,139
[45] Sep. 15, 1981

[54] ULTRASONIC TRANSDUCER PROBE

[75] Inventors: Susumu Enjoji; Koji Saito, both of Tokyo, Japan

[73] Assignee: Tokyo Shibaura Denki Kabushiki Kaisha, Japan

[21] Appl. No.: 14,076

[22] Filed: Feb. 22, 1979

[30] Foreign Application Priority Data

Feb. 22, 1978 [JP] Japan ................................. 53-18534

[51] Int. Cl.³ .................................................. A61B 10/00
[52] U.S. Cl. .................................... 128/660; 128/221
[58] Field of Search .................. 128/660, 663, 24 A, 128/303.19, 749, 753–754, 213, 215, 347, 221, 214 R

[56] References Cited

U.S. PATENT DOCUMENTS

| | | | |
|---|---|---|---|
| 3,017,887 | 1/1962 | Heyer | 128/749 |
| 3,721,227 | 3/1973 | Larson et al. | 128/24 A |
| 4,029,084 | 6/1977 | Soldner | 128/24 A |
| 4,108,165 | 8/1978 | Kopp et al. | 128/24 A |

OTHER PUBLICATIONS

Goldberg, B. B. et al., "UTS Aspiration Biopsy Techniques", *JCU*, vol. 4, No. 2, Apr. 1976, pp. 141–151.
Breyer, B., "Goniometer for Transducer Arrays", *Ultrasound in Med. & Biol.*, vol. 2, No. 2. Feb. 1976, pp. 135–136.

*Primary Examiner*—Robert W. Michell
*Assistant Examiner*—Francis J. Jaworski
*Attorney, Agent, or Firm*—Finnegan, Henderson, Farabow, Garrett & Dunner

[57] ABSTRACT

Disclosed is an ultrasonic transducer probe for extracting tissues or body fluids from internal body organs for diagnostic purposes, in which a cannula guide slot portion is formed separately from a carrier body on which transducer elements are arranged, whereby the cannula guide slot portion may be sterilized independently and fitted in the carrier body as required for use.

12 Claims, 7 Drawing Figures

ULTRASONIC TRANSDUCER PROBE

BACKGROUND OF THE INVENTION

Reference is made to applicants' copending U.S. Application Ser. No. 010,596 for "A Probe For Ultrasonic-Echo Planigraphic Imaging Apparatus," filed on Feb. 7, 1979. That application is directed to similar subject matter.

This invention relates to an ultrasonic transducer probe which may be used in injecting a cannula through a region of the body of a patient to be diagnosed, e.g. in a biopsy.

In a biopsy, tissues or body fluids may be extracted from the kidney, liver and other internal body organs by means of a suitable cannula for diagnostic purposes. Also in the X-ray angiography, a cannula with an injector is pierced into blood vessels and the like to examine morbid changes in a brain, heart, abdominal organs, etc., by injecting a contrast medium. Moreover, amniotic fluid may be extracted from the uterus of a pregnant woman for diagnostic purposes, or blood or medication may be injected into a fetal body.

In all these cases, it is very important to prevent undue damage to essential organs or wrong extraction of tissues.

Accordingly, there is known an apparatus or a combination of an ultrasonic diagnostic apparatus and a cannula in which a transducer element is provided for a cannula guide means, whereby an ultrasonic beam is transmitted into the body of a patient to be examined. With this combination, a sectional image of the interior of the body can be obtained by reproducing the ultrasonic-echo pulses of the beam on a picture screen, and the cannula can be inserted into the body while the positional relationship between the cannula and the internal region to be examined is being observed (U.S. Pat. No. 4,108,165).

In addition, there is known an apparatus in which a tapered cannula guide slot is bored in a carrier of an ultrasonic probe having a plurality of ultrasonic transducer elements arranged thereon. With this apparatus the movement of the cannula can be observed by watching a sectional planar image in the body of a patient. When the ultrasonic transducer elements are driven successively, the direction of the cannula can be optionally selected within a fixed range (U.S. Pat. No. 4,029,084).

Naturally, the cannula to be injected into the patient body is required to be properly sterilized by a suitable method before use. When injecting the cannula into the patient body by using one of the aforesaid prior art ultrasonic transducer probes, however, the cannula will be brought into contact with the inside wall of the cannula guide slot bored through the carrier of the ultrasonic probe, so that the carrier itself will also be required to be disinfected before each use.

Such disinfection of the carrier is generally carried out by a gas sterilization method in which an antiseptic gas is blown upon the carrier so that the gas may be introduced through very small gaps formed at the joint portions of the carrier body 2 or the joint portions between the carrier body and the individual ultrasonic transducer elements. This gas sterilization deteriorates the adhesive strength of an adhesive used for these joint portions and causes exfoliation at these joints. Thus, by repeating such disinfection many times, the components held by the carrier body of the ultrasonic transducer probe may be damaged, and the life of the probe may be shortened. Moreover, in making examinations of several cases by means of a cannula, the carrier body of the probe must be disinfected for each patient. Furthermore, the ultrasonic transducer probe is too complicated in shape to be properly sterilized by gas disinfection.

SUMMARY OF THE INVENTION

The object of this invention is to provide an ultrasonic transducer probe with a cannula guide slot which is capable of proper and easy disinfection or sterilization and which eliminates the fear of damage to the joint portions of transducer elements and the like.

That is, according to this invention, there may be provided an ultrasonic transducer probe comprising a carrier with a plurality of ultrasonic transducer elements arranged in at least one row on an application surface adapted to be located on the body surface of a patient and with a cannula guide slot having one end opening in the application surface, the ultrasonic transducer probe being characterized in that the carrier is composed of a carrier body having a guide cavity spreading out from the application surface toward the opposite surface, and a taper-shaped cannula guide block removably fitted in the guide cavity and having at least one guide slot bored therethrough.

DETAILED DESCRIPTION OF THE PREFERRED EMBODIMENT

Figure 1:
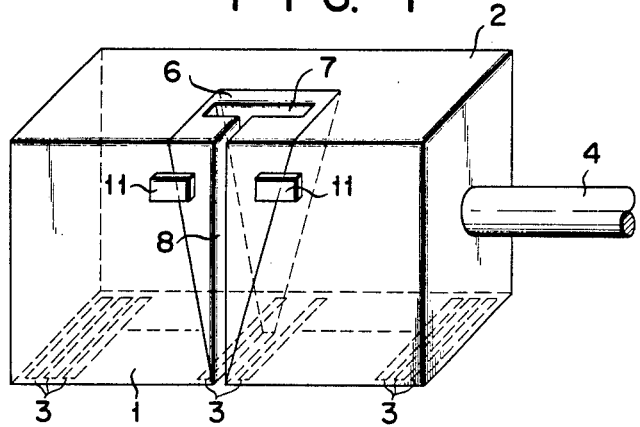
FIG. 1 is a perspective view schematically showing an ultrasonic transducer probe according to this invention.

With an ultrasonic transducer probe according to this invention which comprises a carrier having a plurality of ultrasonic transducer elements arranged in at least one row on an application surface adapted to be located on the body surface of a patient and a cannula guide slot bored through the application surface, the cannula guide slot portion is detachably provided, so that the cannula guide slot portion can be removed from a carrier body. With this probe the cannula guide slot portion which may come into direct touch with the cannula can be properly disinfected or sterilized with ease. That is, according to the invention, hygienic problems may be eliminated by previously sterilizing only the cannula guide slot portion without disinfecting the whole body of the ultrasonic transducer probe by the gas sterilization method or the like, as is the case with the prior art apparatus. After the cannula guide slot position is sterilized, the cannula guide portion may be fitted in the carrier body. Since the carrier guide slot portion is separate from the carrier body, sterilization can be performed easily and properly. Moreover, the cannula guide slot portion alone may be packed in an aseptic condition for disposable use, thereby substantially saving a user the trouble of sterilization as compared with the conventional system. Furthermore, the cannula guide slot portion may be prepared in advance according to the size of a cannula used and easily replaced with new one, providing great facility for practical use. For the carrier body which never comes into direct contact with the cannula, the user on his own judgment can manage with only simple disinfection such as alcohol disinfection.

As for a guide cavity bored through the carrier body, it may be of any shape, provided that it allows a cannula guide block to be fitted therein. In general, however, it should preferably have a shape, such as the shape of a wedge, that spreads out from the application surface of the carrier adapted to be located on the patient's body surface toward the opposite surface. Also, the desirable shape of the guide cavity is to be as simple as possible (e.g. polygonal section) from a hygienic point of view, in order to prevent gathering of dust and to facilitate cleaning. Further, the guide cavity is preferably so formed as to have its one end open substantially in the center of the application surface on which the transducer elements are arranged. Moreover, it is to be desired that the opening portion should be as narrow as possible in order to minimize the vacancy in the row of the transducer elements and to prevent deterioration of picture quality due to a loss in the number of scanning line.

The arrangement of the transducer elements is not specially limited, but may be made in accordance with any prior art form, such as the one which appears in U.S. Pat. No. 4,029,084, for example.

The cannula guide block for guiding the cannula may have any external shape, provided that it can be fitted and securely held in the guide cavity. Generally, however, it should preferably be a tapering shape such as wedge-like, pyramidal or semiconical in connection with the shape of the guide cavity.

As for the cannula guide slot bored through the cannula guide block, it may be of any shape, provided that it is a little wider than the outside diameter of the cannula used. In general, however, it should preferably be triangular (that is, the opening on the cannula inlet side is widened along the direction of the arrangement of the transducer elements, while the outlet side opening forms an aperture nearly as wide as the outside diameter of the cannula) so as to allow free selection of the angle of introducing the cannula, or there may be formed a plurality of elongated holes radially extending from the cannula outlet side to the inlet side. Alternatively, the cannula guide block may be provided with a slit across one side thereof extending along the full length of the slot so that the carrier and the cannula guide block may be removed with only the cannula remaining in the patient body.

Now there will be described some embodiments of this invention with reference to the accompanying drawings.

Referring now to FIG. 1 which schematically shows an ultrasonic transducer probe according to the invention, there are shown an application surface 1 of the probe adapted to be located on the body surface of a patient, a carrier body 2, a number of ultrasonic transducer elements 3 arranged in one row on the application surface 1, a cable 4 for connecting the individual transducer elements to an electric transmitter-receiver section of an ultrasonic diagnostic apparatus, a cannula guide block 6 capable of being removed from the carrier 2, a cannula guide slot 7 with a wide opening on the cannula inlet side (top) and tapered toward the application surface 1 (or cannula outlet side), a slit 8 to allow the cannula to be removed from the carrier body 2 and the cannula guide block 6 in a direction substantially perpendicular to the cannula guide slot 7, and stopper plates 11 for fixing the guide block 6 to the carrier body 2.

Figure 2:
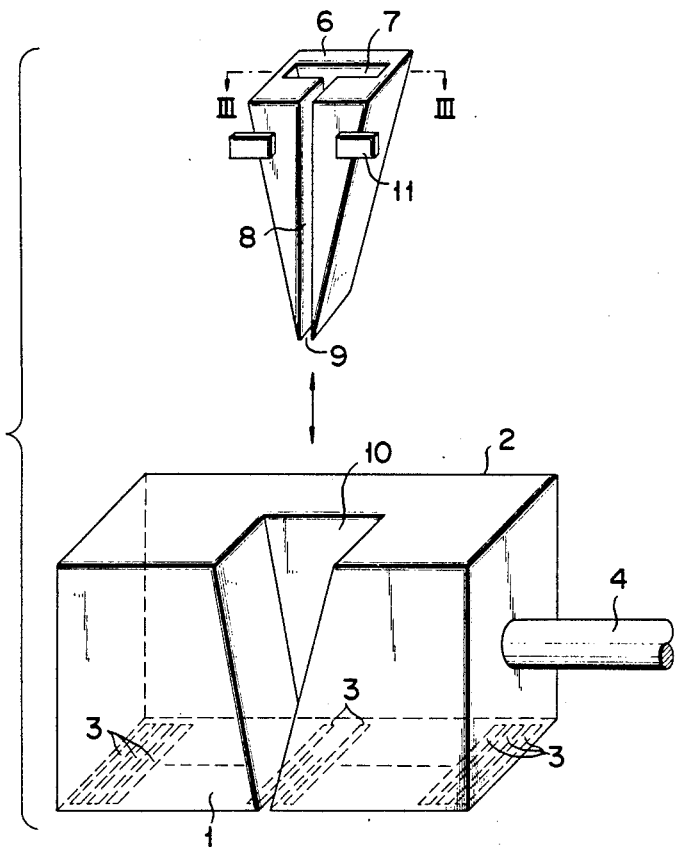
FIG. 2 is a perspective disassembled view showing a carrier body and a cannula guide block of the ultrasonic transducer probe of FIG. 1 which are separated from each other.
Figure 3:
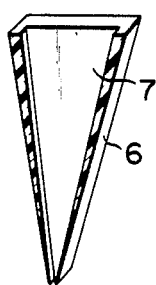
FIG. 3 is a sectional view of the cannula guide block of FIG. 2 as taken along line III—III.

FIG. 2 shows the cannula guide block 6 separated from the carrier body 2 of the ultrasonic transducer probe. The cannula guide block 6, which may be made of plastic, for example, is substantially wedge-shaped externally. Through this cannula guide block 6 are bored the cannula guide slot 7 and slit 8 with widths a little larger than the outside diameter of an optional cannula, extending from the top face of the guide block 6 to the pointed bottom end. The cannula guide slot 7 forms a space with a triangular profile, as shown in FIG. 3. The stopper plates 11 may serve also as handles for attaching and detaching the guide block 6.

Figure 4:
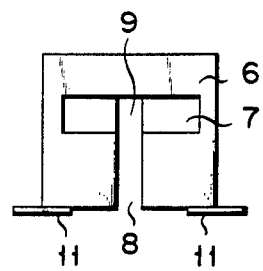
FIG. 4 is a top plan view of the cannula guide block of FIG. 2.

FIG. 4 is a top plan view of the guide block, indicating that the slit 8 extends from the largest opening portion (cannula inlet) to the smallest opening portion (cannula outlet) of the guide slot 7.

As may be seen from FIG. 2, the carrier body 2 is provided with a guide cavity 10 formed of a wedge-shaped space in which the guide block 6 is fitted. On the application surface (bottom) of the carrier body are positioned approximately 100 transducer elements, each having a width of about 1.4 mm, for example, and arranged at intervals of nearly 0.1 mm. Since the guide cavity 10 opens approximately 2 mm wide in the approximate center of the application surface, the opening portion is cleared of those transducer elements. The carrier body 2 may be approximately 200 mm long, 70 mm high and 20 mm wide, for example. The width of the upper opening portion of the guide cavity 10 is about 23 mm.

Now there will be described the operation of the above-mentioned ultrasonic transducer probe.

First, the cannula guide 6, which has previously been sterilized, is fitted in the guide cavity 10. Then, the carrier body 2 of the ultrasonic transducer probe is placed on the body surface of a patient corresponding to a region which requires examination or injection of a contrast medium by means of a cannula, and an ultrasonic sectional image of the region is displayed on a display unit of an ultrasonic diagnostic apparatus, with electric transmission and reception signals transmitted to and from the diagnostic apparatus. Thereafter, the cannula (not shown) is led to the guide slot 7 through the slit 8. The optimum direction of introducing the cannula is then determined from the depth and relative position of the objective region in the patient body, while the user observes the display of the sectional image. Thereupon, the cannula is introduced at a prescribed angle within the guide slot 7, and is actually injected into the patient body. At the same time, an echoic image of the cannula is also displayed on the display unit, whereby a doctor can continually observe the state of the cannula.

Some X-ray photographs may be taken while maintaining the state of the cannula after injection of a contrast medium into the objective region. In this case, the carrier body 2 of the probe must be removed from the body surface of the patient because it may be an obstacle to the photographing. This is one of the reasons why the slit 8 is provided for the guide block 6 fitted in the carrier body 2. That is, the cannula may be removed from the carrier body 2 through the slit 8 by moving the carrier body 2 in the direction at substantially right angles to the direction of the cannula.

Figure 5:
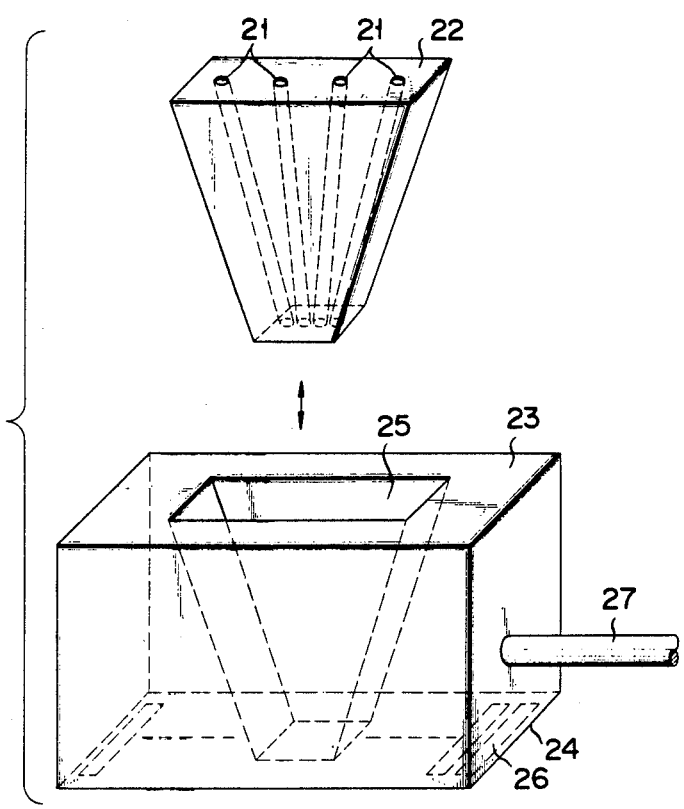
FIG. 5 is a perspective disassembled view showing a modification of the ultrasonic transducer probe of the invention.

FIG. 5 shows a modification of the ultrasonic transducer probe according to this invention, in which a pyramidal cannula guide block 22 is provided with a plurality of cannula guide slots 21 with a circular section somewhat wider than the section of the cannula, the slots 21 radially extending from the bottom to the top of the guide block 22. On the other hand, a carrier body 23 has a guide cavity 25 which can be fitted with the guide block 22, extending from the top to the bottom of the carrier body 23. On the bottom face or an application surface 24 of the carrier body 23 are a number of transducer elements 26 respectively connected to a connecting cable and arranged in one row as is the case with the embodiment of FIG. 2.

Thus, several guide slots 21, as the guide holes for the cannula, are bored through the pyramidal cannula guide block 22 so as to focus on a point in the interior of the patient body, so that the cannula may directly be introduced, as the operator desires, perpendicularly or diagonally into an objective region exposed to an ultrasonic beam by properly selecting one of the guide slots 21 within a fixed range. Moreover, according to the prior art apparatus, the cannula may slip on the surface of a hard tissue in the patient body if it hits against such hard tissue while it is being introduced into the body without a guide, thus advancing the tip of the cannula in an unexpected direction to damage other regions in the body. By using the cannula guide block 22 as shown in FIG. 5, however, the cannula may easily be inserted as one likes without a fear of such damage.

Figure 6:
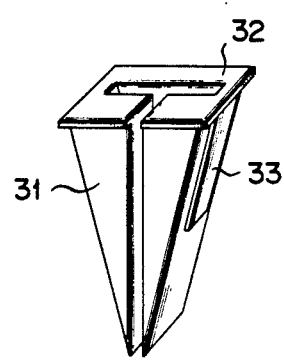
FIGS. 6 and 7 are perspective views showing modifications of the cannula guide block.
Figure 7:
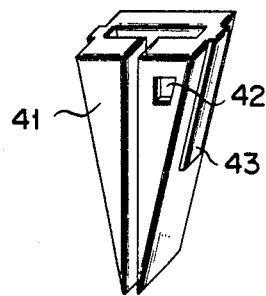

FIGS. 6 and 7 show further modification of the cannula guide block, in which the shapes of the cannula guide slot and the slit communicating therewith are the same as those shown in FIG. 2, except that the handle means and the stopper means of the cannula guide block are modified. That is, in FIG. 6, a flange portion 32 as the handle means is attached to the top face of a cannula guide block 31, and projections 33 as the stopper means to engage the carrier body are formed on both sides of the block 31, respectively. In FIG. 7, an opening 42 as the handle means is bored through the front of a cannula guide block 41, and, for the stopper means, projections 43 similar to the ones shown in FIG. 6 are formed. Naturally, when using the cannula guide blocks 31 and 41 as shown in FIGS. 6 and 7, it is essential to form guide cavities on their respective carrier bodies in shapes fit for their corresponding guide blocks.

It is to be understood that the shape of the cannula guide block may be modified in various manners other than those illustrated without departing from the scope or spirit of this invention. The point is that the cannula guide block be capable of being removed from the carrier body and be securely held within the carrier body.

What we claim is:

1. An ultrasonic transducer probe for use in injecting a cannula through a region of a subject to be examined comprising:
   a carrier with a plurality of ultrasonic transducer elements arranged proximate to an application surface of said carrier adapted to be positioned on the body surface of the subject,
   a guide cavity formed in said carrier, said guide cavity extending to said application surface to form an application opening in said application surface proximate to said transducer elements,
   a cannula guide block sized to removably and securedly fit within said guide cavity and having at least one guide slot bored therethrough for guiding the cannula, said guide slot communicating with the application opening in said application surface but not communicating with any portion of said carrier itself when said cannula guide block is fit within said guide cavity, and
   a slit communicating with said guide slot along its full length and further communicating with the exterior of said carrier to permit the removal of said ultrasonic transducer probe from the subject after a cannula is inserted through said probe and into the body of the subject,
   whereby the cannula guide block can be removed from said carrier and sterilized independently of said carrier.

2. The ultrasonic transducer probe of claim 1 whereby said cannula guide block does not require sterilization by the gas sterilization method.

3. The ultrasonic transducer probe of claim 1 wherein said cannula guide block is formed of a readily disposable material.

4. The ultrasonic transducer probe of claim 1 wherein said guide slot is wider at the cannula inlet side opposite to said application opening and tapered toward the outlet side.

5. The ultrasonic transducer probe according to claim 4 wherein said cannula guide block has a substantially wedge-shaped external form and said guide cavity is formed of a space that substantially corresponds to the shape of said cannula guide block.

6. The ultrasonic transducer probe of claim 5 further comprising a projection, formed on at least one side of said cannula guide block, for engagement with said carrier.

7. The ultrasonic transducer probe of claim 5 further comprising a flange formed on the top surface of said cannula guide block and seatable against the top surface of said carrier.

8. The ultrasonic transducer probe of claim 7 further comprising handle means for inserting and removing said cannula guide block from said carrier.

9. The ultrasonic transducer probe according to claim 8 wherein said handle means is a flange portion on the top face of said cannula guide block.

10. The ultrasonic transducer probe according to claim 8 wherein said handle means is an opening bored on one side of said cannula guide block.

11. The ultrasonic transducer probe of claim 5 further comprising guide cavities formed on said carrier body and projections formed on said cannula guide member and engageable with respective guide cavities.

12. An ultrasonic transducer probe for use in injecting a cannula through a region of a subject to be examined comprising:
   a carrier with a plurality of ultrasonic transducer elements arranged proximate to an application surface of said carrier adapted to be positioned on the body surface of the subject,
   a guide cavity formed in said carrier, said guide cavity extending to said application surface to form an application opening in said application surface proximate to said transducer elements, and a cannula guide block sized to removably and securedly fit within said guide cavity and having a plurality of radially extending guide slots bored therethrough for guiding the cannula, said guide slots being focused to intersect at one point beyond said application surface to allow a user to introduce the cannula from a selected radial position and communicating with the application opening in said application surface but not communicating with any portion of said carrier itself when said cannula guide block is fit within said guide cavity, whereby the cannula guide block can be removed from said carrier and sterilized independently of said carrier.

* * * * *